(12) United States Patent
Nair et al.

(10) Patent No.: US 7,416,777 B2
(45) Date of Patent: Aug. 26, 2008

(54) DIAPER INCLUDING INK-PRINTED SUBSTRATE WEB

(75) Inventors: Radhakrishnan Janardanan Nair, Kobe (JP); Shunketsu Sue, Kobe (JP)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 11/713,530

(22) Filed: Mar. 2, 2007

(65) Prior Publication Data

US 2007/0154690 A1 Jul. 5, 2007

Related U.S. Application Data

(62) Division of application No. 10/439,546, filed as application No. PCT/US00/34905 on Dec. 21, 2000, now Pat. No. 7,205,041.

(51) Int. Cl.
*B32B 27/14* (2006.01)
*B32B 3/00* (2006.01)

(52) U.S. Cl. ............. 428/195.1; 442/64; 604/358; 604/385.23

(58) Field of Classification Search ............ 428/195.1; 442/64; 604/358, 385.23; 427/258
See application file for complete search history.

(56) References Cited

U.S. PATENT DOCUMENTS

| | | | |
|---|---|---|---|
| 3,867,171 A | 2/1975 | Ellsworth |
| 4,421,826 A | 12/1983 | Ohlson et al. |
| 4,507,342 A | 3/1985 | Kielbania |
| 4,686,260 A | 8/1987 | Lindemann et al. |
| 4,695,278 A | 9/1987 | Lawson |
| 4,795,454 A | 1/1989 | Dragoo |
| 4,795,675 A | 1/1989 | Dunn et al. |
| 4,811,428 A | 3/1989 | Waldman et al. |
| 4,961,964 A | 10/1990 | Dahlgren |
| 4,969,951 A | 11/1990 | Loike et al. |
| 4,988,344 A | 1/1991 | Reising et al. |
| 4,988,345 A | 1/1991 | Reising |
| 5,017,423 A | 5/1991 | Bossmann et al. |
| 5,219,969 A | 6/1993 | Uhl et al. |
| 5,240,767 A | 8/1993 | Umezu et al. |
| 5,405,650 A | 4/1995 | Boulanger et al. |
| 5,431,643 A | 7/1995 | Ouellette et al. |
| 5,458,590 A | 10/1995 | Schleinz et al. |
| 5,503,076 A | 4/1996 | Yeo |
| 5,695,855 A | 12/1997 | Yeo et al. |
| 5,853,859 A | 12/1998 | Levy et al. |
| 4,795,454 C1 | 6/2001 | Dragoo |
| 2003/0207091 A1 | 11/2003 | Nair, et al. |

FOREIGN PATENT DOCUMENTS

EP 0 120 579 A2 3/1984
WO WO 99/60973 * 12/1999

OTHER PUBLICATIONS

PCT US00/34905 filed Jul. 4, 2002, Radhakrishnan Janardanan Nair, et al.

* cited by examiner

*Primary Examiner*—Norca Torres-Velazquez
(74) *Attorney, Agent, or Firm*—Laura L. Whitmer; Matthew P. Fitzpatrick; Ken K. Patel

(57) ABSTRACT

A disposable diaper including an ink-printed substrate web exhibiting ink rub-off resistance. The substrate web is printed with an ink composition to form an ink film on the substrate web. The ink film is coated with a coating composition to form a coating film on the ink film. At least one of the ink composition and the coating composition forms a cross-linked structure within the film thereof and forms a cross-linked structure with the other composition between the ink film and the coating film. A method for making the diaper includes the steps of printing and coating the ink film.

12 Claims, 4 Drawing Sheets

DIAPER INCLUDING INK-PRINTED SUBSTRATE WEB

CROSS-REFERENCE TO RELATED APPLICATIONS

This application is a division of co-pending application Ser. No. 10/439,546 filed on 16 May 2003, which is the National Stage of International Application No. PCT/US00/34905, filed Dec. 21, 2000, now U.S. Pat. No. 7,205,041 the substances of which are hereby incorporated in their entirety herein by reference.

FIELD OF THE INVENTION

The present application relates to a disposable diaper including an ink-printed substrate web exhibiting improved ink rub-off resistance and a method for making such a diaper.

BACKGROUND OF THE INVENTION

An ink-printed substrate web is broadly used in various consumer products. For example, in personal care products such as disposable garments, it is often desired to provide graphic designs printed with an ink on the outside of the disposable garment to enhance the aesthetic appearance and the consumer acceptance and to make the diaper look more like a conventional baby garment. For this purpose, an ink-printed substrate web, which could be a polymeric film or a nonwoven fibrous web, is used for the outermost layer of the disposable garment.

One problem of the ink-printed substrate web is poor ink rub-off resistance. Ink rub-off is typically caused by abrasion of the ink with other substances such as clothes of the wearer of a disposable garment, a carpet on the floor or the like. One method of solving this problem is to print the graphics on an inner substrate web such as a film or a nonwoven to be covered by an outer substrate web. As the printed surface of the inner substrate web is covered with the outer substrate web, the printed graphic on the inner substrate web does not get abraded directly with other contacting substrates and ink rub-off does not occur. While the substrate web covering the printed surface of the inner substrate web contributes to reduce the abrasion of the printed surface, the outer substrate web tends to hide the graphics printed on the inner substrate web to make the graphics to have hazy appearance. The fibers in a nonwoven if a nonwoven is used for the outer substrate web appear very distinctively on the printed graphics when covering a dark colored graphics. This also limits the vivid color expression of the graphic.

Yet another way of circumventing the problem of ink rub-off is to put the printed surface inside and the non-printed surface outside such that the printed surface is not abraded. In this case, however, the substrate web itself printed with the graphics tends to hide the graphics. Thus, there is a need for an ink-printed substrate web having an ink-printed surface which can be exposed to abrasion, yet exhibiting good ink rub-off resistance.

Attempts have been made to improve ink rub-off resistance on a substrate web, e.g., in U.S. Pat. No. 5,458,590 issued on Oct. 17, 1995 to Schleintz et al. titled "INK-PRINTED, LOW BASIS WEIGHT NONWOVEN FIBROUS WEBS AND METHOD", U.S. Pat. No. 5,695,855 issued on Dec. 9, 1997 to Yeo et al. titled "DURABLE ADHESIVE-BASED INK-PRINTED POLYOLEFIN NONWOVENS", and U.S. Pat. No. 5,853,859 issued on Dec. 29, 1998 to Levy et al. titled "ROOM TEMPERATURE LATEX PRINTING". However, the existing art may not provide all of the advantages and benefits of the present invention.

SUMMARY OF THE INVENTION

A disposable diaper includes an ink-printed substrate web exhibiting ink rub-off resistance. The substrate web is printed with an ink composition to form an ink film on the substrate web. The ink-printed substrate web is coated with a coating composition to form a coating film on the ink film. At least one of the ink composition and the coating composition forms a cross-linked structure within the film thereof and forms a cross-linked structure with the other composition between the ink film and the coating film. A method for making a disposable diaper including the ink-printed substrate web exhibiting ink rub-off resistance is also provided.

These and other features, aspects, and advantages of the invention will become evident to those skilled in the art from a reading of the present disclosure.

BRIEF DESCRIPTION OF THE DRAWINGS

While the specification concludes with claims particularly pointing out and distinctly claiming the invention, it is believed that the present invention will be better understood from the following description of preferred embodiments taken in conjunction with the accompanying drawings in which:

DETAILED DESCRIPTION OF THE INVENTION

Figure 1:
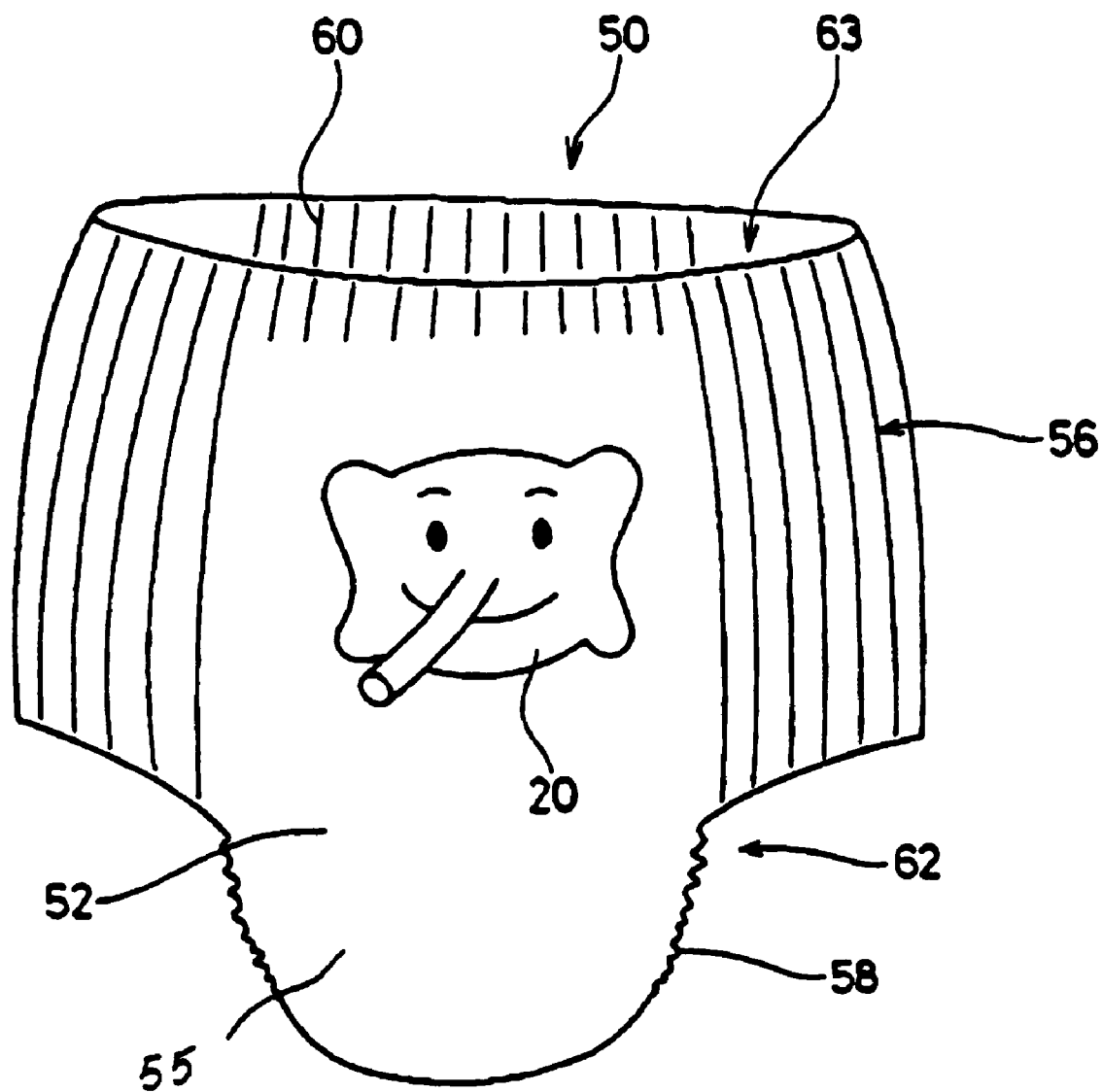
FIG. 1 is a back view of one embodiment of a disposable pull-on diaper having an ink-printed substrate web with exemplary graphics.

All percentages herein are by weight of compositions unless specifically stated otherwise. All ratios are weight ratios unless specifically stated otherwise. As used herein, the term "comprising" means that other steps and other ingredients which do not affect the end result can be added. This term encompasses the terms "consisting of" and "consisting essentially of."

The ink-printed substrate web of the present invention exhibits improved rub-off resistance. The ink-printed substrate web is preferably used for consumer products, such as personal care products including disposable absorbent articles.

As used herein, the term "absorbent article" refers to devices which absorb and contain body exudates, and, more specifically, refers to devices which are placed against or in proximity to the body of the wearer to absorb and contain the various exudates discharged from the body.

The term "disposable" is used herein to describe absorbent articles which are not intended to be laundered or otherwise restored or reused as an absorbent article (i.e., they are intended to be discarded after a single use and, preferably, to be recycled, composted or otherwise disposed of in an environmentally compatible manner). The disposable absorbent article could include, but not limited to, a diaper for infants, a diaper for adult incontinent persons, incontinence briefs, incontinence garments, diaper holders and liners, feminine hygiene garments, training pants, and the like. Further, the ink-printed substrate web of the present invention may be used for any type of consumer products.

The ink-printed substrate web should have excellent ink rub-off resistance. An ink-printed substrate web with poor ink rub-off resistance is problematic because the removal of the ink from the printed substrate web contributes to a deterioration in the quality of the ink-printed graphics on the substrate web or a transfer of the ink from the ink-printed substrate to other substrates.

As used herein, "ink" refers to any liquid composition or components thereof applied onto the substrate web and which remains thereon in a visible pattern even though components of the ink may evaporate.

The term "rub-off" refers to the transfer of color from the surface of a printed substrate web. Ink rub-off is typically due to abrasion. Abrasion refers to the ability to remove ink from a substrate web by mechanically scuffing the ink from the surface of the substrate web.

Ink rub-off can be a problem especially when printed on polyolefin polymer based substrate web such as a nonwoven made of polyolefin fibers. Polyolefin homo-polymers such as polypropylene, polyethylene have very low surface energy as compared to conventional substrates like cellulose, nylon or poly (ethylene terephthalate). This makes the ink composition difficult to adhere to the surface of the polyolefin polymer based substrate web. Further, unmodified homopolymer polyolefin polymers such as polypropylene and polyethylene do not have any chemical reactive site for the ink composition to anchor with the polymer. Thus, unmodified polyolefin polymer based substrate web typically provides insufficient binding force for an ink composition to resist the friction applied to the ink-printed substrate web due to its inherently poor surface energy and/or chemical structure while the polyolefin polymer based substrate web is beneficial in several aspects compared with other commercial polymers, such as cost, processability into a form of fibers or films, or softness in the form of fibers or films. While polyolefin polymers can be modified to have a reactive site through copolymerization, radiation grafting or the like, these polymers are not commercially available yet.

Another aspect causing ink rub-off problem can be an ink itself. Typically, an ink composition comprises a coloring agent, a binder polymer, a solvent and other additives. The coloring agent such as a pigment is dispersed in a binder polymer dissolved in a solvent. The ink composition forms an ink film on the substrate web which in turn consists of several sub-layers of resin mixed with pigment. If the binding between these sub-layers is insufficient to bind each sublayers, these sublayers get removed gradually during abrasive contact with other substrates. Thus, the poor binding between the sub-layers of the ink film also contributes to the poor rub-off resistance of the ink on the substrate web.

The ink-printed substrate web of the present invention comprises three key elements; a substrate web to be printed, an ink composition used for printing the substrate web, and a coating composition used for coating the printed ink. The substrate web may be applied with a corona discharging treatment prior to printing the ink composition on the substrate web to raise a surface energy of the substrate web. The ink composition is used to print the substrate web and to form an ink film layer on the substrate web. The coating composition is used to coat the ink-printed area of the substrate web and to form a coating film layer on the ink film. The coating film is preferably a transparent such that the ink film layer is visible through the coating film. However, the coating film may be translucent as far as the ink film layer is visible.

Herein, the term "ink film" or "ink film layer" refers to a solid ink film structure which is left behind by evaporating a solvent in the ink composition. The term "coating film" or "coating film layer" refers to a solid coating film structure which is left behind by evaporating a solvent in the ink composition.

The ink composition comprises a first binder polymer and a first hardener, and the first binder polymer and the first hardener form a cross-linked structure within the ink film layer such that the binding between each sublayer of the ink film improves. The coating composition comprises a second binder polymer and a second hardener and the second binder polymer and the second hardener form a cross-linked structure within the coating film layer such that the binding between each sublayer of the coating film improves. The term "sublayer" refers to the thinnest unit of the film layer which contains all the ingredients of the film layer as a whole. The first binder polymer of the ink composition may form a cross-linked structure with the second hardener of the coating composition such that the cross-linked structure is formed between the ink film and the coating film to strengthen the binding therebetween. Alternatively, the second binder polymer of the coating composition may form a cross-linked structure with the first hardener of the ink composition such that the cross-linked structure is formed between the ink film and the coating film to strengthen the binding therebetween.

Preferably, the first binder polymer of the ink composition forms a cross-linked structure with the second hardener of the coating composition and the second binder polymer of the coating composition may form a cross-linked structure with the first hardener of the ink composition. Most preferably, the first binder polymer of the ink composition forms a cross-linked structure with the first hardener of the ink composition and with the second hardener of the coating composition and the second binder polymer of the coating composition forms a cross-linked structure with the first hardener of the ink composition and with the second hardener of the coating composition. When the ink composition comprises the first binder polymer and the first hardener and the first hardener can form a cross-linked structure with the second binder polymer of the coating composition, the coating composition may not necessarily contain the second hardener.

Alternatively, when the coating composition comprises the second binder polymer and the second hardener and the second hardener can form a cross-linked structure with the first binder polymer of the ink composition, the ink composition may not necessarily contain the first hardener. If either composition lacks a hardener, the coating layer preferably comprises a binder polymer and a hardener while the ink composition comprises a binder polymer without a hardener because the coating film faces outside of the substrate web and should be tough to resist abrasion. As far as a binder polymer and a hardener can form a cross-linked structure, any type of binder polymer and any type of hardener may be used. Further, the first binder polymer and the first hardener may be the same as the second binder polymer and the second hardener respectively.

The substrate web to be printed with an ink composition may include any type of substrate, such as a nonwoven, a woven fabric, a film, or a laminate comprising thereof. In one embodiment, the substrate web to be printed with an ink composition may be a nonwoven web which may be used for consumer products such as an outermost layer of disposable absorbent articles. The ink-printed nonwoven web is preferable for the use of the outermost layer of disposable absorbent articles to provide a cloth-like feeling and aesthetically appealing appearance.

Preferably, the ink-printed surface of the nonwoven web is exposed outside of disposable absorbent articles. The ink-printed nonwoven may be laminated with a liquid impermeable film comprising a polymeric film which serves as a barrier to liquid in disposable absorbent articles. The ink-printed nonwoven may be laminated outside of the polymeric film such that the ink-printed surface is exposed outside of disposable absorbent articles.

Alternatively, the ink-printed nonwoven may be laminated outside of the polymeric film such that the ink-printed surface comes in contact with the polymeric film. If the ink-printed nonwoven has liquid impermeability or is treated to be liquid impermeable, the ink-printed liquid impermeable nonwoven may be used for a liquid impermeable barrier of disposable absorbent articles without requiring an additional polymeric film. The substrate web to be printed with an ink may be selected depending on the purpose of the use in consumer products. Exemplary substrate webs are a multi-layered nonwoven, a stretchable nonwoven, a liquid impermeable polymeric film, a liquid permeable polymeric film, a vapor permeable polymeric film, a vapor impermeable polymeric film, a stretchable film, a multi-layered film, a laminate comprising a nonwoven and a polymeric film, a woven fabric, or the like. A nonwoven web is particularly preferable for use of consumer products such as an absorbent article.

The nonwoven web may comprise any type of fibers such as natural fibers (e.g., wood or cotton fibers), synthetic fibers (e.g., polyolefins, polyamides, polyester fibers), or a combination of natural and/or synthetic fibers. The fibers may have any shape such as a circular cross section shape or a non-circular cross section shape, preferably a non-circular cross section shape. The fiber denier can be any of range depending up on the end use. Polyolefin polymer based nonwoven is beneficial in several reasons such as cost, processability into a form of fibers, or softness in the form of fibers.

The nonwoven web can be made by any known methods. It may be made by bonding of web-like arrays of fibers or filaments. The web may be made from fibers of discrete length ranging from few millimeter to few meters by carding or wet or air laying process or they may be produced by laying or blowing filaments as they are being melt extruded. The fabrics made by these latter process are commonly known as spunbonded or spunlaid and melt-blown nonwoven webs. A spunbonded nonwoven web may be defined generically as continuous filament fibrous structures which are made in the form of fabrics, sheets or tapes and are prepared from synthetic polymers in a process integrated with fiber manufacture. A melt-blown nonwoven web is a fibrous structure produced by extruding a polymer melt through a die into a high velocity stream of hot air to produce fine or super fine fibers which are deposited on a moving screen after quenching. A carded nonwoven web is made from carded fibers. The preferred polymers for the production of filaments or fibers for making the nonwoven web are polyolefins such as polyethylene or polypropylene. In one embodiment, a preferred nonwoven web for the use of the outermost layer of disposable absorbent articles may be a spunbonded nonwoven comprising polypropylene fibers with a basis weight of between about 9 g/m$^2$ and about 110 g/m$^2$. An exemplary nonwoven web for the use of the present invention is supplied by Mitsui Chemical in Japan under the designation code of PC-0220 (commercial name: Mitsui Copoly PP Nonwoven 20 gsm).

The poor surface energy of the substrate web is one of the reasons for poor surface adhesion of the ink composition to the substrate web. As mentioned above, unmodified polyolefin polymers have very low surface energy because of their non polar nature. It is very difficult to make an ink or a lacquer bond effectively to the surface of the polyolefin polymer based substrate web. For example the surface energy of freshly made polypropylene based substrate web is in the range of about 29 dynes/cm. For a good surface adhesion of the printing ink, the surface energy of the substrate web is preferably appreciably higher than the printing ink. The substrate web surface energy is preferably about 40 dynes/cm or higher, more preferably about 42 dynes/cm or higher for a solvent-based ink.

The substrate web is processed by a corona discharging treatment to increase the surface energy of plastic substrate web. In corona discharging treatment, electrons are accelerated into the surface of the substrate web causing the polymer molecular chains on the surface of the substrate web to rupture, producing multiplicity of open ends and free valances. The free valances are then able to form carbonyl groups with the oxygen atoms from the ozone created by the electric discharge. This increases the surface energy of the substrate web and improves adhesion to the printing ink.

In the corona discharging treatment, the substrate web is fed into a controlled air-gap between two electrodes, one of which is energized with high voltage electrical field and the other of which is grounded. As high voltage power is applied across the electrode, the air-gap and the substrate, the air in the gap becomes ionized from the acceleration of electrons to form a gaseous conductor comprising corona. The ionized air-gap induces an electron avalanche which in turn creates oxidative molecules such as ozone. The ozone oxidizes the surface of the substrate web and increases the surface energy and surface adhesion. An important factor which needs to be controlled is the extent of polymer chain rupture which occurs during the corona discharging treatment to avoid any adverse effect to the substrate web. For example, when the substrate web is a nonwoven web which is porous, the corona discharging treatment needs to be controlled to avoid any adverse effect on the mechanical integrity of the nonwoven web. A fine optimization of the corona discharging treatment in terms of the treatment power, surface energy and material mechanical integrity needs to be maintained. The corona discharging treatment can be made at corona discharging treatment power of between about 20 W·m$^2$/min. and about 60 W·m$^2$/min., preferably between about 40 W·m$^2$/min. and about 60 W·m$^2$/min., more preferably between about 40 W·m$^2$/min. and about 58 W·m$^2$/min. The corona discharging treatment can be applied by, e.g., Sherman Corona Treater supplied by Sherman Treaters.

The substrate web applied with corona discharging treatment is then processed by a printing process. The printing process may be any known process such as flexographic printing, ink-jet printing, screen printing, or rotogravure printing. Flexographic printing is preferable because of the suitability of the method in printing soft substrates as well as considering the speed of production and cost factors. Flexographic printing process uses a raised printing surface made of a flexible material to transfer an ink image to the substrate web. The flexible surface is able to transfer a good image even to a rough substrate web. The printing may be made in either mono-color or multi-color. A liquid ink is used which may be solvent or water based, and dries mainly by evaporation.

The ink composition comprises two components; a first base component and a first hardening component. The first base component comprises a coloring agent, a binder polymer (first binder polymer), a solvent and other additives if desired. The first hardening component comprises a hardener (first hardener) and a solvent and other additives if desired. Instead of the first base component, the first hardening component may contain a coloring agent. Alternatively, both first base component and first hardening component may contain a coloring agent. Based upon weight of the total ink composition, suitable addition ranges for the first base component ranges from about 60% to about 100%, preferably from about 70% to about 95%, more preferably from about 80% to about 95%. Based upon weight of the total ink composition, suitable addition ranges for the first hardening component ranges from about 0% to about 40%, preferably from about 5% to about 30%, more preferably from about 5% to about 20%. A suitable first base component and a suitable first hardening component are preferably in the form of a liquid at room temperature (i.e., a temperature of about 20° C.).

The coloring agent of the first base component may be generally termed as pigments which refers to insoluble color matter used in finely dispersed forms. The pigments may be dyes, organic pigments or inorganic pigments. Exemplary organic pigments may include: C.I. Pigment Yellow 1, C.I. Pigment Yellow 3, C.I. Pigment Yellow 13, C.I. Pigment Red 5, C.I. Pigment Red 7, C.I. Pigment Red 12, C.I. Pigment Red 112, C.I. Pigment Red 122, C.I. Pigment Blue 1, C.I. Pigment Blue 2, C.I. Pigment Blue 16, C.I. Vat Blue 4, C.I. Vat Blue 6, or Carbon black. Exemplary inorganic pigments may include: titanium dioxide (e.g., Pigment White 6), carbon black (e.g., Pigment Black 7), iron oxides, ferric oxide black (e.g., Pigment Black 11), chromium oxide, or ferric ammonium ferrocyanide. Exemplary dyes may include: Solvent Yellow 14, Dispersed Yellow 23, Metanil Yellow, Solvent Red 111, Dispersed Violet 1, Solvent Blue 56, Solvent Orange 3, Solvent Green 4, Acid Red 52, Basic Red 1, Solvent Orange 63, or Jet Black. Based upon weight of the total first base component, the suitable addition range for the coloring agent is from about 1% to about 49%, preferably from about 3% to about 30% more preferably from about 5% to about 20%.

The binder polymer of the first base component preferably has at least two or more functional groups (open reactive groups) such as hydroxyl groups which can react with the hardener of the first hardening component to form a high molecular weight cross-linked film of the ink when printed on the substrate. If the binder polymer and the hardener are tri-functional, the resulting cross-linked molecules will have higher molecular weight. The binder polymer of the first base component may be epoxy, polyols, styrene-butadiene, ethylene vinyl acetates, ethylene vinyl chlorides, acrylates, styrene acrylates, pure phenolics, polyvinyl butyral resin, and mixtures thereof. Epoxy or polyols are preferable. Based upon weight of the total first base component, suitable addition range for the binder polymer is from about 10% to about 50%, preferably from about 10% to about 40%, more preferably from about 10% to about 30%.

Epoxy resins may be defined as glycidyl ethers of polyhydroxy compounds. Typical polyhydroxy compounds which may be used include bisphenol A (common name for 4,4'-isopropylidene bisphenol), ring substituted bisphenol A, resorcinal, hydroquinone, phenol-formaldehyde novolac resins, aliphatic diols such as ethylene glycol, propylene glycol, 1,4-butanediol, 1,6 hexanediol glycerol, poly(oxyethylene) glycol, poly(oxypropylene)glycol, linear glycidyl epoxy resins derived from dihydric phenols, and the like.

Polyols may be any organic hydroxy compound, having a functionality of two or more that is soluble in the solvents employed. Such polyhydroxy compounds can include simple aliphatic polyols, polyether polyols, phenolic resins, and mixtures of these. Exemplary polyols may include polyhydroxy functional straight or branched chain saturated or unsaturated hydrocarbons, optionally comprising one or more oxy or ester moieties and optionally comprising one or more heterocyclic atoms, aromatic and/or heterocyclic rings, the heterocyclic atom(s) being selected preferably from N, O and S. Suitable polyol reactants include many commercially available materials well known to the skilled of the art. Preferred chain-extendible, crosslinkable polyols include epoxydiol adducts which can be provided as the reaction product of a suitable diepoxide with a suitable diol, and polyurethane resin with hydroxyl groups.

The solvent of the first base component may comprise a single component of solvent, or a mixture solvent comprising two or more components of solvent. The type of the solvent is preferably determined considering the solubility of the binder polymer and/or the drying time of the ink in terms of the printing machinery drying efficiency. Preferably, the solvent used in the first base component is a mixture of solvents. The solvent system may consist of a mixture of one or more of the following components: water; alcohols such as 2-propanol, 1-propanol, and ethanol; acetates such as ethyl acetate and propyl acetate, butyl acetate; glycols such as propylene glycol; and glycol ethers such as propylene glycol mono methyl ether.

The ink composition also may contain other additives, such as pH control agents, viscosity modifiers, defoamers, dispersants, printing press hygiene control agents, preservatives, and/or corrosion control agents. Waxes is preferable as an additive to improve the slip properties of ink. Exemplary waxes may include: natural waxes such as carnauba wax, beeswax, Japan wax, shellac wax; petroleum waxes such as slack wax, scale wax, ceresin wax; synthetic waxes such as polyethylene, polytetrafluroethylene, fatty acid amides. Cellulose nitrate, shellac, silica, etc. can also be added as an additive.

The hardener of the first hardening component forms a cross-linked structure with the binder polymer of the first base component for the ink composition. The ink composition forms an ink film on the substrate web which in turn consists of several sub-layers of resin mixed with pigment. The cross-linked structure contributes to bind each sub-layer such that each sublayer does not get readily removed during abrasive contact with other substrates to improve rub-off resistance of the ink composition. Further, the hardener of the first hardening component preferably forms a cross-linked structure with the binder polymer of the second base component for the coating composition explained hereinbelow to bind the outermost sublayer of the ink composition and the innermost layer of the coating composition which contact to one another. Based upon weight of the total first hardening component, the suitable addition range for the hardener is from 0% to about 40%, preferably from about 5% to about 30%, more preferably from about 5% to about 15%.

The hardener may be a solution polymer consisting of a cationic polyamine-epichlorohydrin polymer, primary diamine curing agent, or polyisocyanate with free isocyanate groups. Primary diamine curing agent is preferably used with the binder polymer consisting of epoxy resins. Polyisocyanate with free isocyanate groups is preferably used with the binder polymer consisting of polyols.

Suitable polyisocyanates may be any organic polyisocyanate having 2 or more NCO groups per molecule. Suitable such polyisocyanates include, for example, 2,4-toluenediisocyanate, 2,6-toluenediisocyanate, hexamethylene diisocyanate, p,p'-diphenylmethanediisocyanate, p-phenylenediisocyanate, hydrogenated methylene diphenyldiisocyanate, naphthalene diisocyanate, dianisidine diisocyanate, polymethylene polyphenyl-isocyanate, mixtures of one or more polyisocyanates and the like.

The solvent of the first hardening component may comprise a single component of solvent, or a mixture solvent comprising two or more components of solvent. The type of the solvent is preferably determined considering the solubility of the hardener and/or the drying time of the ink in terms of the printing machinery drying efficiency. Preferably, the solvent used in the first hardening component is a mixture of solvents. The solvent system may consist of a mixture of one or more of the following components: water; alcohols such as 2-propanol, 1-propanol, and ethanol; acetates such as ethyl acetate and propyl acetate, butyl acetate; glycols such as propylene glycol; and glycol ethers such as propylene glycol mono methyl ether.

Typically the first base component for the ink composition and the first hardening component for the ink composition are mixed to form an ink composition prior to printing. Depending on the ink composition, the binder polymer and/or the hardener used, the speed of cross-linking varies. An optimized ink composition should have a pot life ranging from 8-10 hours. After the two components are mixed to form an ink composition, the ink is printed on the substrate web. The substrate web are then dried to evaporate the solvents of the ink composition. The chemical curing of the printed ink will happen during the aging period under a normal room temperature (i.e., 25° C.). The aging temperature and time to achieve complete curing will vary according to the hardener and ink composition used. The speed of the curing can also be increased by the use of catalysts. Alternatively, the curing may be performed after the coating composition is applied on the ink composition. Thus, the ink-printing is made on a substrate web. The ink composition forms a film on the substrate web which in turn consists of several sub-layers of resin mixed with pigment. The cross-linked structure of the ink composition binds each sublayers such that the sublayers are readily not removed during abrasive contact with other substrates.

The ink composition printed on the substrate web is further coated with a coating composition. The coating composition covers the outermost sublayer of the ink composition with some pigments on the surface which might get rubbed-off during a frictional contact with an abrasive surface. To prevent or at least reduce such rub-off or removal of colored ink from the ink film on the substrate web, a transparent over print coating is provided to cover the ink composition. The coating composition forms a high molecular weight cross-linked transparent film over the ink film printed on the substrate web. The coating composition forms a high molecular weight cross-linked structure within the coating composition, and preferably forms a cross-linked structure with the ink composition. This will create a secured and strong transparent coating film which protects the ink film sublayers from getting rubbed-off. Further, because the coating composition does not contain any pigments or contains only minimal amount of pigments to maintain the transparency of the coating, the coating composition forms a smooth surface which further reduces the coefficient of friction of the surface of the coating when come in abrasive contact with other surfaces to improve the ink rub-off resistance.

The coating composition comprises two components; a second base component and a second hardening component. The two component system may be the same as that of the ink composition except that the coating composition does not contain a coloring agent in it. The second base component comprises a binder polymer (second binder polymer), a solvent, and other additives if desired. The second hardening component comprises a hardener (second hardener), a solvent, and other additives if desired. The binder polymer of the second base component and the hardener of the second hardening component are selected to form a cross-linked structure within the coating composition. The binder polymer of the second base component is preferably selected to form a cross-linked structure with the hardener of the first hardening component of the ink composition. The hardener for the second hardening component is also preferably selected to form a cross-linked structure with the binder polymer of the first base component of the ink composition. This allows to form a cross-linked structure between the outermost layer of the ink composition and the innermost layer of the coating composition and to provide a binding strength between the ink layer and the coating layer, thereby improving the rub-off resistance of the ink composition. The binder polymer of the second base component may be selected from the component which is chemically similar to, preferably the same as the binder polymer of the first base component for the ink composition. The hardener of the second hardening component for the coating composition may be selected from the component which is chemically similar to, preferably the same as the hardener of the first base component for the ink composition. Alternatively, the binder polymer and the hardener for the coating composition may be selected from the component which is different from the binder polymer and the hardener for the ink composition. The solvent for the second base component and the second hardening component may be any type of solvent, preferably similar to, more preferably the same as the solvent for the first base component and the first hardening component for the ink composition, respectively.

Based upon weight of the total second base component, the suitable addition range for the binder polymer is from about 10% to about 50%, preferably from about 10% to about 40%, more preferably from about 10% to about 30%. Based upon weight of the total second hardening component, the suitable addition range for the hardener is from 0% to about 40%, preferably from about 5% to about 30%, more preferably from about 5% to about 15%.

A preferable example of the two component ink system comprises polyurethane polymer with hydroxyl groups in the chain end as well as in the branches for a binder polymer and polyisocyanate for a hardener. The binder polymer along with a coloring agent and suitable printing additives are dissolved in a suitable solvent mixture to form a first base component. The hardener is also dissolved in a suitable solvent mixture to form a first hardening component. The first base component and the first hardening component are then mixed prior to printing. The ink composition thus formed is printed on the substrate and over coated with a transparent coating composition which comprises two components. A preferable example of the two component coating system comprises the same components as the ink composition except that the coating composition does not contain the coloring agent. The printed and over coated substrate is then dried by evaporating the solvent and then aged for cross-linking in the ink composition and the coating composition and between the ink composition and the coating composition.

Referring to FIG. 1, there is shown one embodiment of a consumer product utilizing an ink-printed substrate web with exemplary graphics. FIG. 1 shows a disposable diaper which is a pull-on diaper 50. The pull-on diaper 50 is generally pulled onto the body of the wearer by inserting the legs into the leg openings 62 and pulling the article up over the waist. Alternatively, the disposable diaper may be a conventional open-type taped diaper with an adhesive tape fastening system and/or a mechanical tape fastening system.

Figure 2:
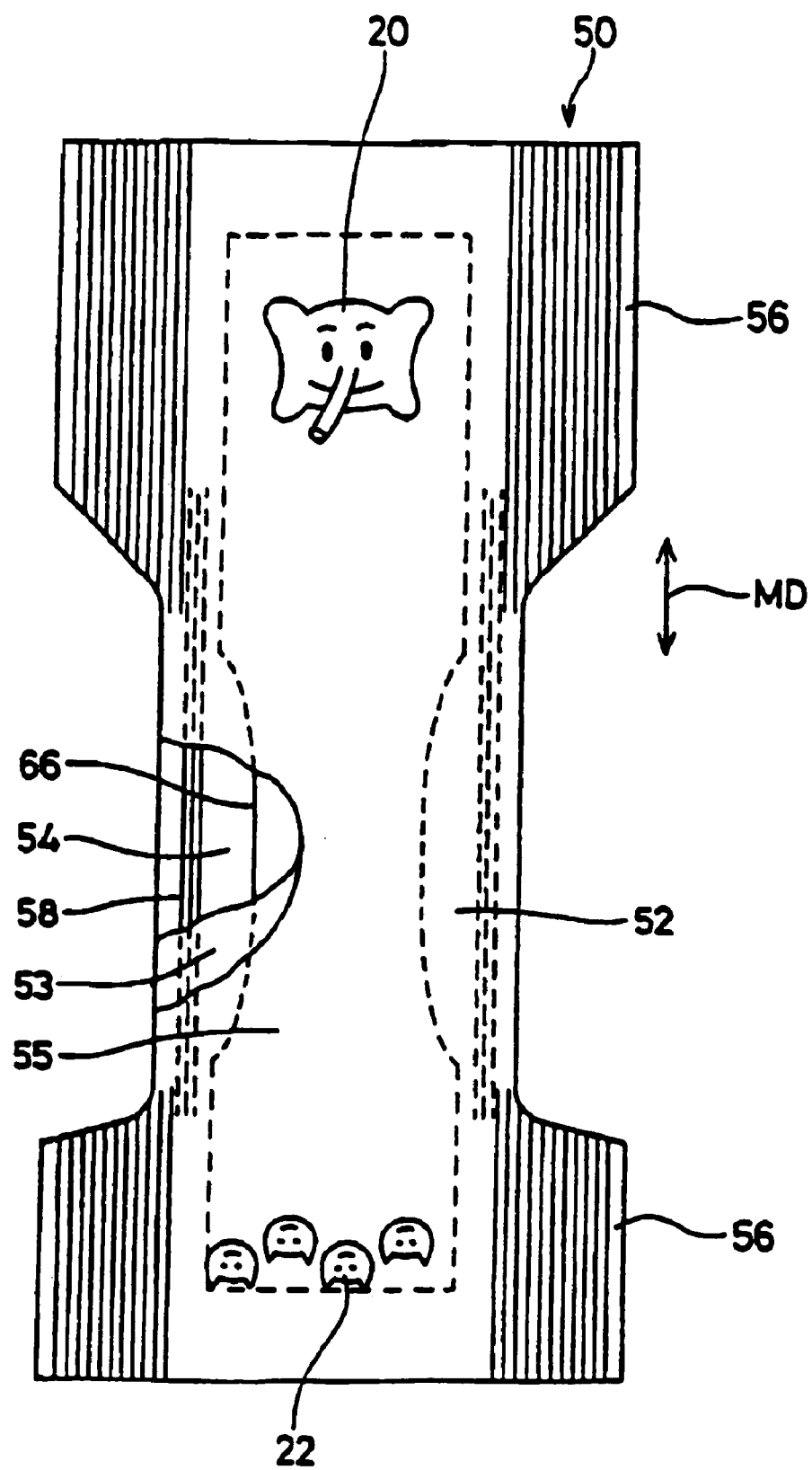
FIG. 2 is a simplified plan view of the pull-on diaper of FIG. 1 in its flat, uncontracted state prior to formation.

Referring to FIG. 2 as well, the diaper 50 generally comprises a backsheet 52, a topsheet 54 and an absorbent layer 66 located between the backsheet 52 and the topsheet 54. The topsheet 54 is located to be placed facing the body or nearest the body when the diaper is worn and is generally provided with a liquid permeable region so that body exudates can flow through the topsheet 54 to the absorbent layer 66. The backsheet 52, which is placed away from the body during wear, is typically liquid impermeable so that outer clothing or other articles are not wetted by the body exudates. The backsheet 52 comprises a microporous polymer film 53 and a layer of nonwoven material 55 laminated to the outside of the microporous film 53 in which case there is provided a more cloth-like and garment-like feel than is typically obtained with a film backsheet only. The backsheet 52 is printed with graphics 20. The diaper 50 has elastically extensible side panels 56 provided to ensure more comfortable and contouring fit by initially conformably fitting the pull-on diaper 50 to the wearer and sustaining this fit throughout the time of wear well past when it has been loaded with exudates. Leg elastics 58 and waist elastic region 60 are also provided to enhance the fit around the legs and waist, respectively. The side panels 56 are joined at seams to form a waist opening 63 and leg openings 62. As will be understood by those of skill in the art, many other features for disposable absorbent articles are within the scope of the present invention. For example, barrier cuffs as described in Lawson and Dragoo U.S. Pat. Nos. 4,695,278 and 4,795,454 are a desirable feature for disposable absorbent articles. In addition, skin care-type topsheets that are provided with lotion thereon for the purpose of reducing skin irritation and chafing are a desirable feature herein.

The graphics 20, 22 are printed on the backsheet 52. Preferably, the graphics 20, 22 are printed on the outer surface (garment facing surface) of the nonwoven 55 of the backsheet. The nonwoven 55 is preferably applied with a corona discharging treatment to raise its surface energy to improve adhesion of an ink composition to the surface of the nonwoven as described above. The nonwoven 55 is then printed with an ink composition and coated with a coating composition as described above. Alternatively, the graphics 20, 22 may be printed on the inner surface (i.e., microporous film facing surface) of the nonwoven 55, or may be printed on the outer surface (i.e., nonwoven film facing surface) of the microporous film 53.

FIG. 1 shows the back view of the diaper 50 with an exemplary graphic 20 positioned in about the upper region of the nonwoven 55 of the backsheet 52, on the back side of the diaper 50. In FIG. 2, there is shown a simplified plan view of an embodiment of a disposable absorbent article in its flat, uncontracted state prior to formation. In this embodiment, the graphic 20 is shown in the back region of the diaper with graphics 22 additionally shown in the front region. The graphics 20 and 22 are preferably registered to be positioned on the predetermined position of the diaper 50 such that the graphics 20 and 22 appear on the same position on each diaper without significant variation. Each diaper may be printed with the same pattern of the registered graphics. Alternatively, each diaper may be printed with two or more different patterns of the registered graphics. The graphics 20 and/or 22 may be printed with a mono-color ink or multi-color inks. Further, the printing may be made on other portions of the diaper such as a landing zone for a fastening tape, a barrier cuff, a back ear portion, and/or a front ear portion.

Referring to FIG. 2, the topsheet 54 and the backsheet 52 have length and width dimensions generally larger than those of the absorbent core 66. The topsheet 54 and the backsheet 52 extend beyond the edges of the absorbent core 66 to thereby form the periphery of the diaper 50. The topsheet 54, the backsheet 52, and the absorbent core 66 may be assembled in a variety of well known configurations.

The absorbent core 66 may be any absorbent member which is generally compressible, conformable, non-irritating to the wearer's skin, and capable of absorbing and retaining liquids such as urine and other certain body exudates. The absorbent core 66 may be manufactured in a wide variety of sizes and shapes (e.g., rectangular, hourglass, "T"-shaped, asymmetric, etc.) and from a wide variety of liquid-absorbent materials commonly used in disposable diapers and other absorbent articles such as comminuted wood pulp which is generally referred to as airfelt. Examples of other suitable absorbent materials include creped cellulose wadding; chemically stiffened, modified or cross-linked cellulosic fibers; tissue including tissue wraps and tissue laminates; absorbent foams; absorbent sponges; superabsorbent polymers; absorbent gelling materials; or any equivalent material or combinations of materials. The configuration and construction of the absorbent core 66 may vary (e.g., the absorbent core may have varying caliper zones, a hydrophilic gradient, a superabsorbent gradient, or lower average density and lower average basis weight acquisition zones; or may comprise one or more layers or structures). Further, the size and absorbent capacity of the absorbent core 66 may also be varied to accommodate wearers ranging from infants through adults. However, the total absorbent capacity of the absorbent core 66 should be compatible with the design loading and the intended use of the diaper 50.

The topsheet 54 is preferably positioned adjacent the inner surface of the absorbent core 28 and is preferably joined thereto and to the backsheet 52 by attachment means (not shown) such as those well known in the art. In a preferred embodiment of the present invention, the topsheet 54 and the backsheet 52 are joined directly to each other in the diaper periphery and are indirectly joined together by directly joining them to the absorbent core 66 by any suitable attachment means.

The topsheet 54 is preferably compliant, soft feeling, and non-irritating to the wearer's skin. Further, the topsheet 54 is preferably liquid pervious permitting liquids (e.g., urine) to readily penetrate through its thickness. A suitable topsheet 54 may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. The topsheet 54 can be rendered hydrophilic by treating it with a hydrophilic finishing oil or a surfactant. Suitable methods for the treatment for the topsheet 54 include spraying the topsheet 54 material with surfactant and immersing the material into the surfactant. A more detailed discussion of such a treatment and hydrophilicity is contained in U.S. Pat. No. 4,988,344 entitled "Absorbent Articles with Multiple Layer Absorbent Layers" issued to Reising, et al. on Jan. 29, 1991 and U.S. Pat. No. 4,988,345 entitled "Absorbent Articles with Rapid Acquiring Absorbent Cores" issued to Reising on Jan. 29, 1991, each of which is incorporated by reference herein. Alternatively, the topsheet 24 may be a carded nonwoven material which is formed by fibers treated with hydrophilic finishing oil.

The backsheet 52 is that portion of the diaper 50 which is generally positioned away from the wearer's skin and which prevents the exudates absorbed and contained in the absorbent core 66 from wetting articles which contact the diaper 50 such as bedsheets and garments. Thus, the backsheet 52 is impervious to liquids (e.g., urine) and is preferably manufactured from a thin plastic film, although other soft, flexible liquid impervious materials may also be used. (As used herein, the term "flexible" refers to materials which are compliant and will readily conform to the general shape and contours of the human body.) While the backsheet 52 is impervious to liquids, the backsheet 52 permits moisture to escape from the diaper 50. The backsheet 52 may comprise a breathable microporous film 53 and an outer nonwoven sheet 55.

The microporous film 53 may comprise any known material being moisture pervious and liquid impervious. For example, the microporous film 53 may comprise a breathable microporous film composed of a thermoplastic resin and inorganic fillers dispersed in the thermoplastic resin. Suitable thermoplastic polymers include polyolefins such as polyethylenes, including liner low density polyethylene (LLDPE), low density polyethylene (LDPE), ultra low density polyethylene (ULDPE), high density polyethylene (HDPE), or polypropylene and blends thereof with the above and other materials. The inorganic filler and the thermoplastic polymer are blended together to form a homogeneous mixture in a suitable mixing extruder, or in a separate preliminary compounding step. The mixture is then cast or blown into a film. The obtained film is stretched at least in one direction to impart breathability on the substantially entire area or a portion of the film.

The nonwoven outer sheet 55 may be joined with at least a portion of the garment-facing surface of the microporous film 53. The nonwoven sheet 55 may cover all or substantially all of the garment-facing surface of the microporous film 53, or may cover only discrete predetermined portions. In a preferred embodiment, the nonwoven web of the nonwoven sheet 55 covers all or substantially all of the microporous film 53 in order to provide the diaper with a cloth-like look and feel.

The nonwoven web comprised in the nonwoven sheet 55 may comprise natural fibers (e.g., cotton or wood fibers), or may comprise fibers of polyolefins such as polyethylene and polypropylene, polyester, or any combination of such fibers. Polyolefin fibers are preferable. Further, the nonwoven may be carded, spunbond, meltblown or air-through bonded or have any other characteristic or be manufactured in any manner known in the art. An especially preferred nonwoven is a spunbonded nonwoven made of 100% polypropylene fibers such as Mitsui Copoly PP nonwoven 20 gsm (designation code: PC-0220) supplied by Mitsui Chemical in Japan.

A moisture vapor transmission rate of the backsheet is important in reducing the incidence of heat rash and other skin problems associated with high humidity conditions. A moisture permeable substrate web printed with an ink composition typically has less moisture permeability than before being printed. This is because an ink film layer printed on the substrate web tends to fill the open apertures or micropores formed in the moisture permeable substrate web to close the open apertures or micropores. The reduction of moisture permeability of the substrate web caused by an ink printing is more apparent in the moisture permeable substrate web formed by a microporous film than by a nonwoven because the size of micropores of a microporous film is much smaller than that of apertures of a nonwoven and get readily closed or narrowed by the ink composition. Therefore, it is preferable to make an ink printing on a nonwoven substrate to secure a required moisture permeability. The ink-printed nonwoven is joined to the microporous film prior to printing or after printing such that the ink-printed surface is exposed outside and the opposite side of the ink-printed surface faces the microporous film. Such a laminate comprising an ink-printed nonwoven and a microporous film enhances the aesthetic appearance and the consumer acceptance while maintaining a moisture permeability and liquid impermeability.

A preferable uppermost amount of the ink composition applied in the ink-printed area on the nonwoven may be not more than about 10 $g/m^2$, preferably not more than about 6 $g/m^2$, more preferably not more than about 4 $g/m^2$. A preferable lowermost amount of the ink composition applied on the nonwoven may be not less than about 0.05 $g/m^2$, preferably not less than about 0.1 $g/m^2$, more preferably not less than about 0.3 $g/m^2$. Herein the term "ink-printed area" refers to the area in which the ink composition is applied to a substrate web to make a visible object on the substrate web. The amount of the ink composition is the total amount of the ink compositions applied in the ink-printed area. Namely, if the ink-printed area is printed with a single color ink composition, the amount is that of the single color ink composition. If the ink-printed area is printed with three different color ink compositions, the amount is the total amount of each different color ink composition. If the ink-printed area is further coated with a coating composition, a preferable uppermost total amount (basis weight) of the ink-composition and the coating composition may be not more than about 10 $g/m^2$, preferably not more than about 6 $g/m^2$, more preferably not more than about 4 $g/m^2$. A preferable uppermost amount of the coating composition may be not more than 9.95 $g/m^2$, preferably not more than about 9.9 $g/m^2$, more preferably not more than about 9.7 $g/m^2$. In order for the ink-printed nonwoven not to significantly reduce the moisture permeability of the laminate, the amount of the ink composition applied on the nonwoven is not preferably beyond the uppermost amount above. If the ink-printed area is further coated with a coating composition, the total amount of the ink-composition and the coating composition preferably is not preferably beyond the uppermost total amount above.

A moisture vapor transmission rate of the laminate of the ink-printed nonwoven and a microporous film in the maximum ink-printed portion is not less than about 50%, preferably not less than about 60%, more preferably not less than about 70% of a moisture vapor transmission rate of the laminate before being printed. Moisture vapor transmission rate ("MVTR") is a characteristic measure of breathability. MVTR refers to the permissible moisture volume from one side of the substrate web to the other side of the substrate web per area unit (e.g., per square meter) and per time unit (e.g., per one day). The MVTR of a substrate web may be measured by the Cup Test method. This method is described as follows. A known amount of calcium chloride (CaCl2) is put into a stainless steel container which is a cylindrical container with a diameter of 30 mm and a depth of 50 mm. The CaCl2 with water level measurement useful herein may be purchased from Wako Pure Chemical Co., Ltd. A substrate web test sample is placed on the top of the container, and the container is tightly closed with a cap and screws. The cap has a hole through it and thus moisture outside the container can diffuse into the container through the substrate web test sample. The container with the substrate web test sample is then placed in a constant temperature (40° C.) and humidity environment (75% relative humidity) for a fixed period of time. The amount of moisture absorbed by the CaCl2 in the container is a measure of the moisture permeability of the substrate web. A test sample is taken to have a circular shape with the diameter of 4 cm (the center 3 cm diameter portion is used for measurement and the periphery portion is used to anchor the test sample to equipment for measurement). When a moisture vapor transmission rate of the laminate comprising a nonwoven and a microporous film before being printed is measured, a test sample may be taken from the laminate before an ink printing is made onto the laminate in the manufacturing process. Instead, the laminate before being printed may be represented by a non-printed portion of the laminate assembled into a final product such as an absorbent article. When a moisture vapor transmission rate of the laminate of the ink-printed nonwoven and a microporous film in the maximum ink-printed portion is measured, a test sample is taken from the laminate after an ink printing is made onto the laminate in the manufacturing process. Instead, the test sample may be taken from a final product. Herein, "maximum ink-printed portion" means the portion of the laminate in which the rate of the ink-printed area to the area of a specified area of the substrate web is maximum. The specified area of the substrate web can be defined by the method for measurement. When the moisture vapor transmission rate is measured by the above method, the specified area corresponds to the area of the substrate web for measurement and is the circular portion with the diameter of 3 cm.

A bending force of the ink-printed nonwoven used for, e.g., a backsheet, a side ear panel, a landing zone for a fastening system, or a tape for a fastening system for an absorbent article is important for providing consumers, i.e., caregiver and wearer, with softness and/or flexibility. A portion of the nonwoven printed with an ink composition typically becomes less soft/flexible than before being printed due to the ink composition forming a film layer on the nonwoven which gives some stiffness to the nonwoven. If the ink-printed area is further coated with a coating composition, the softness and/or flexibility of the ink-printed nonwoven further reduces.

In order for the ink-printed nonwoven to have sufficient softness and/or flexibility, the amount of the ink composition applied on the nonwoven is not preferably beyond the uppermost amount above (i.e., the amount of the ink composition is preferably not more than about 10 g/m$^2$, preferably not more than about 6 g/m$^2$, more preferably not more than about 4 g/m$^2$). If the ink-printed area is further coated with a coating composition, the total amount of the ink-composition and the coating composition preferably is not preferably beyond the uppermost total amount above (i.e., the total amount of the ink composition and the coating composition is preferably not more than about 10 g/m$^2$, preferably not more than about 6 g/m$^2$, more preferably not more than about 4 g/m$^2$).

The ink-printed area of the nonwoven may have an average bending force value of not more than about 50 mgf·cm$^2$/cm, preferably not more than about 40 mgf·cm$^2$/cm, and more preferably not more than about 35 mgf·cm$^2$/cm. The lower limit of the bending force may be determined arbitrarily by the skilled in the art in balance with the requirement of the amount of the ink composition for clear graphics and the total amount of the ink composition and the coating composition. As used herein, "bending force" means the mechanical property defined as the slope of M-K curve shown in FIG. 5. M is bending momentum per unit width and K is curvature. Bending force can be measured by the method described herein below.

Figure 3:
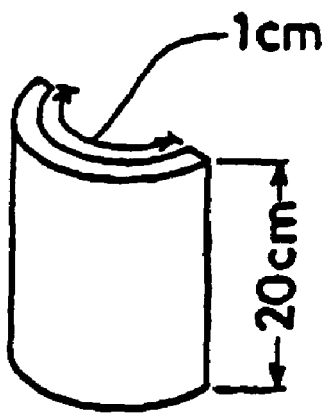
FIGS. 3 and 4 are schematic diagrams of the bending property measurement.
Figure 4:
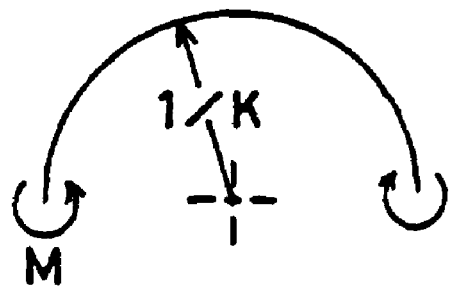
Figure 5:
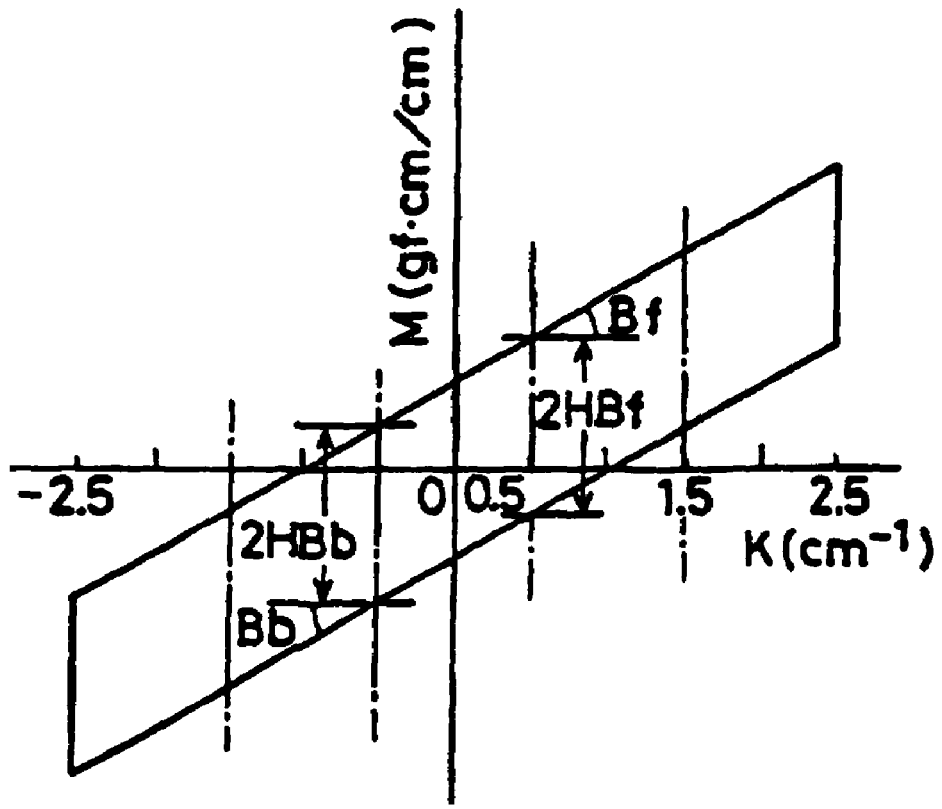
FIG. 5 is a graph showing the bending hysteresis curve.

A bending tester, KES-FB2, Kato Tech. Co Ltd., is used to measure bending force. The deformation mode is a pure bending between the curvature $K=-2.5$ cm$^{-1}$ and $2.5$ cm$^{-1}$. The effective dimension for the measurement is 20 cm in length and 1 cm in width (rectangular). Therefore, the test sample is taken to have at least 20 cm in length and 1 cm in width to include the maximum ink-printed portion of the substrate web. In this case, the specified area for determination of the maximum ink-printed portion is 20 cm in length and 1 cm in width. The test sample is bent as shown in FIGS. 3 and 4. The bending rate is 0.5 cm$^{-1}$/sec. As a result, the bending hysteresis curve as shown in FIG. 5 is obtained by the measurement. The horizontal axis shows the curvatures K cm$^{-1}$ and the vertical axis shows the bending moment per unit width M (gf·cm/cm). The bending force is calculated as follows:

Bending Force=$(Bf+Bb)/2$ where Bf and Bb are the slopes of the hysteresis curves between $K=0.5$ cm$^{-1}$ and $1.5$ cm$^{-1}$ and $K=-0.5$ cm$^{-1}$ and $-1.5$ cm$^{-1}$ respectively.

Measurements are carried out in the MD and CD directions of the same web test sample. The average bending force is the mean value of the above bending force obtained from the measurements about the MD and CD directions of the test sample.

A fuzz level of the ink-printed nonwoven used for, e.g., a backsheet, a side ear panel, a landing zone for a fastening system, or a tape for a fastening system for an absorbent article is important for reducing fuzz of fibers on the ink-printed nonwoven. The fuzzy fibers can collect dust into the fuzzy fibers to contaminate the surface of the nonwoven and provide consumers with an impression of poor appearance. Further the ink-printed nonwoven printed with multi-color loses clearness and/or sharpness of the multi-color images due to the fuzzed fibers. Because the ink composition which forms an ink film layer tends to provide binding to the fibers of the nonwoven, the fibers have a reduced tendency to become fuzzy. The ink composition which can form a cross-linked structure is also useful to provide a binding force to the fibers. When the ink composition is further coated with a coating composition which can form a cross-linked structure within the coating composition, the binding force of the fibers becomes high to further reduce the fuzz of the fibers. When the ink composition and the coating composition form a cross-linked structure to each other, the binding force of the fibers is further enhanced.

In order for the ink-printed nonwoven to have a reduced fuzz level, the amount of the ink composition applied on the nonwoven is not preferably below the lowermost amount above (i.e., the amount of the ink composition is preferably not less than about 0.01 g/m$^2$, preferably not less than about 0.05 g/m$^2$, more preferably not less than about 0.07 g/m$^2$). When the ink composition is not less than these lowermost ranges, it is also possible to provide an aesthetic appearance and a consumer acceptance by the ink-printed graphics.

The ink-printed area of the nonwoven may have a Fuzz Level (FL) of not more than about 0.25 mg/cm$^2$, preferably not more than about 0.2 mg/cm$^2$, and more preferably from about 0.15 mg/cm$^2$. The method for measuring the Fuzz Level of nonwoven webs or layers is explained hereinbelow.

Figure 6:
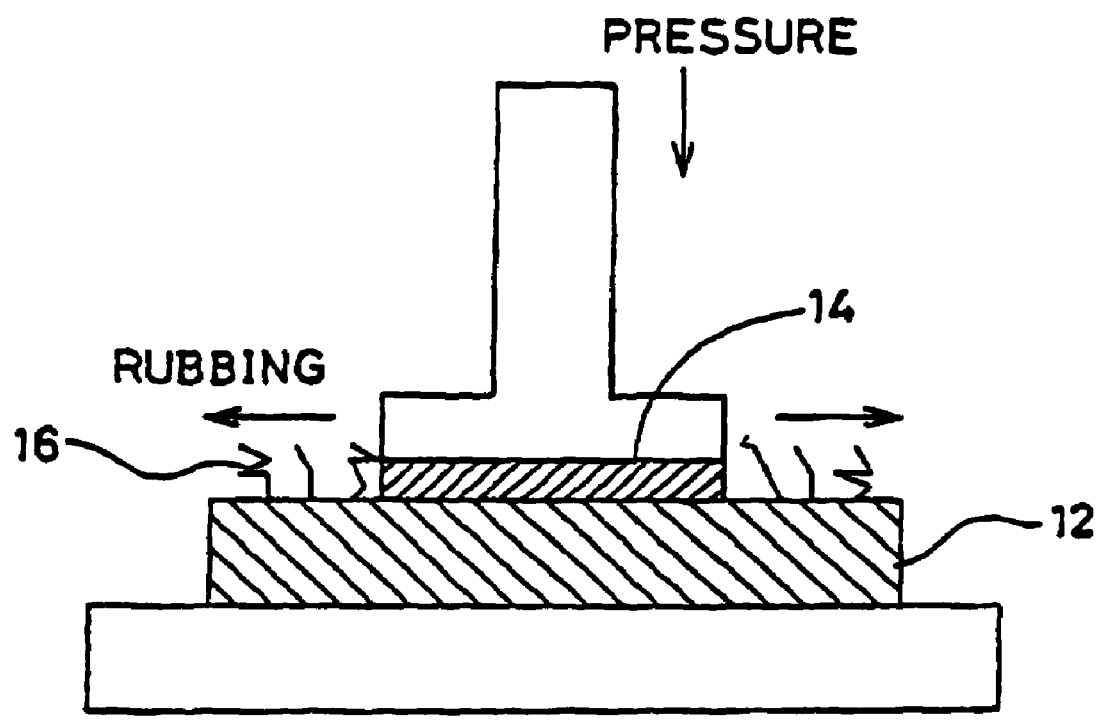
FIG. 6 is a schematic diagram explaining the fuzz level measurement.

To measure the quantity of untangled fibers that protrude from the surface of the test sample, as shown in FIG. 6, the face of the sample 12 is rubbed against the face of sandpaper 14 for 29 seconds at 0.7 Hz to cut or loose the untangled fibers 16. 2000 gf/cm$^2$ of pressure is applied to the sample 12. An example of the equipment is shown in FIG. 6. The cut fibers produced by this action are collected by a removal tape and quantified with an analytical balance. The fuzz level is defined as the weight of the fibers collected per unit area (mg/cm$^2$).

An example of equipment available is Sutherland Ink Rub Tester. 2000 gf/cm$^2$ of pressure is applied to the test sample. This apparatus abrades a 4 cm×11 cm piece of test sample with a 15 cm×5.1 cm piece of sandpaper (Matelite K224 Cloth Sandpaper Grit 320-J, Norton Co., Troy, N.Y.). Therefore, the test sample is taken to have at least 11 cm in length and 4 cm in width to include the maximum ink-printed portion of the substrate web. In this case, the specified area for determination of the maximum ink-printed portion is 11 cm in length and 4 cm in width. The rub cycle is 20 times at 0.7 cycle/sec. The fibers (fuzz) are removed using two 15 cm×5.1 cm pieces of removal tape (3M No. 3187 Trans Tape, Cincinnati, Ohio) from both the sandpaper and the test sample.

An ink-printed substrate of the present invention such as an ink-printed nonwoven used for, e.g., a backsheet, a side ear panel, a landing zone for a fastening system, or a tape for a fastening system for an absorbent article should have minimal ink rub-off amount during the use of the ink-printed nonwoven. The ink rub-off amount is not more than 0.05 mg/cm$^2$, preferably not more than 0.03 mg/cm$^2$, more preferably not more than 0.01 mg/cm$^2$.

The ink rub-off amount is measured by using a rubbing procedure and equipment for rubbing as described in Japanese Industrial Standard test method for color fastness to rubbing. The method used is JIS L 0849. There are two types of apparatus indicated in the method; Rubbing tester I and Rubbing tester II. Rubbing tester II (Gakushin Type) is used herein. The test sample size used for the test is 220 mm length and 30 mm width. The sample should be cut in such a way that the maximum ink-printed portion of the substrate comes in the middle of the sample. It should be ensured that the maximum ink-print portion comes in contact with the white cotton swatch attached to the rubbing finger when rubbed. The 100 mm×20 mm area of the test sample which is being rubbed by the white cotton swatch attached to the rubbing finger should contain the maximum ink-printed portion. Therefore, the determination of the maximum ink-printed position is 100 mm×20 mm. In cases where the specified sample size could not be cut, small size sample can be attached to an un-printed test sample of the same substrate of the specified test sample size. There are two different procedures indicated in the method; Dry rubbing test and Wet rubbing test. Wet rubbing test is used herein. In Wet rubbing test, the water should be a distilled water.

The amount of ink rubbed off to a standard white cotton swatch is measured using UV spectroscopy. First, a known weight of coloring agents such as pigments or colorants corresponding to the colors used for printing is dissolved in a solvent. The solvent needs to be selected in such a way that there is no UV absorption of the solvent in the wavelength range where the coloring agent has the UV absorption. Any solvent which can dissolve the coloring agent and which do not interfere with the UV absorption spectra of the coloring agent can be used. Exemplary solvents used for the current test is N-N dimethylformamide or o-Chlorophenol. The UV absorption spectra of the solution is recorded using a UV spectrophotometer UV-3101PC of Shimadzu Corporation, Japan in the range of 300 nm-850 nm. The concentration of the solution is adjusted to get spectra with in the measurable range. Second, the ink rubbed off to the cotton swatch area of 20 mm×20 mm is dissolved in the selected solvent by immersing the cotton swatch in the solvent. The swatch should be immersed in the solvent for time period and at a temperature required to dissolve the coloring agent completely from the cotton swatch to the solvent.

The UV spectra of the dissolved coloring agent is measured in the range of 300 nm-850 nm. In the case of multi-colored printing, different absorption range corresponding to the colors used will appear in the spectra. The amount of each coloring agent which is dissolved from the cotton swatch can be estimated by comparing with the spectra of the solution for the known amount of coloring agent. If the UV absorption spectra of the coloring agent solution dissolved from the white cotton swatch gives well defined absorption peaks with well defined base line, the area under these peaks can be compared with the area under peak of the UV absorption spectra of the solution for the known amount of coloring agent. If the peaks are not well defined and if the base line can not be drawn, differential of the spectra can be used to get accurate results. The amount of ink rubbed-off to the white cotton swatch is expressed in terms of weight of the rubbed-off ink per unit area of the white cotton swatch (e.g., mg/cm$^2$).

EXAMPLES

The following examples further describe and demonstrate the preferred embodiments within the scope of the present invention. The examples are given solely for the purpose of illustration, and are not to be construed as limitations of the present invention since many variants thereof are possible without departing from its spirit and scope.

Example 1

A spunbonded nonwoven web comprising polypropylene fibers with basis weight of 33 g/m$^2$ is used as a substrate web. It is continuously supplied and applied with corona discharging treatment by Sherman Corona Treater supplied by Sherman Treaters at the corona discharging power of 58 W·m2/min. An ink composition is a red based ink composition and comprises a first base component and a first hardening component as specified below respectively. The first base component and the first hardening component are mixed prior to printing to form the ink composition. The corona treated nonwoven is printed with the ink composition by using a flexographic printing machinery at a speed of approximately 150 m/min. The amount of the ink composition applied is 1 g/m$^2$. A coating composition comprises a second base component and a second hardening component as specified below respectively. The second base component and the second hardening component are mixed prior to coating to form the coating composition. The ink composition printed on the nonwoven web is coated with the coating composition with 2 g/m$^2$. The printed and over coated nonwoven is then dried by evaporating the solvent and is then aged at room temperature (i.e., 25° C.) for 24 hours.

| Ink Composition | | |
|---|---|---|
| First base component | | 90% |
| First hardening component | | 10% |
| First base component | | |
| Binder Polymer | Polyurethane resin | 5.0% |
| | Polyvinyl butyral resin | 7.5% |
| Coloring Agent | C.I. Pigment Red 48-3 | 10.0% |
| Solvent | 1-propanol | 41.6% |
| | 2-Propanol | 1.2% |
| | Ethyl acetate | 4.7% |
| | Propyl acetate | 20.5% |
| | Ethyl alcohol | 2.6% |
| Additives | Polyethylene wax | 3.3% |
| | Cellulose Nitrate | 0.6% |
| | Shellac | 3.0% |
| First hardening component | | |
| Hardener | Polyisocyanate | 37.5% |
| Solvent | Ethyl acetate | 62.5% |

| Coating Composition | | |
|---|---|---|
| Second base component | | 90% |
| Second hardening component | | 10% |
| Second base component | | |
| Binder Polymer | Polyurethane resin | 12.5% |
| | Polyvinyl butyral resin | 8.0% |
| Solvent | 1-propanol | 14.1% |
| | 2-Propanol | 51.4% |
| | Ethyl acetate | 2.7% |
| | Propyl acetate | 6.9% |
| Additives | Polyethylene wax | 3.4% |
| | Silica | 1.0% |
| Second hardening component | | |
| Hardener | Polyisocyanate | 37.5% |
| Solvent | Ethyl acetate | 62.5% |

Example 2

The spunbonded nonwoven web of Example 1 is printed with a red based ink, a blue based ink and an yellow based ink in its order, and then coated with the coating composition. The red based ink composition is the same as Example 1. The blue based ink composition contains C.I. Pigment Blue 15-4 as a coloring agent instead of C.I. Pigment Red 48-3 of the red based ink composition of Example 1 while the rest of the components of the blue based ink composition is the same as those of the red based ink composition of Example 1. The yellow based ink composition contains C.I. Pigment Yellow 14 as a coloring agent instead of C.I. Pigment Red 48-3 of the red based ink composition of Example 1 while the rest of the components of the yellow based ink composition is the same as those of the red based ink composition of Example 1. The total amount of the three ink compositions applied is 1 g/m². The rest of the conditions are the same as Example 1.

Example 3

An extrusion laminate of a carded nonwoven comprising polypropylene fibers with 18 g/m² and a microporous breathable film comprising liner low density polyethylene and calcium carbonate fillers is used as a substrate web. A mixture of liner low density polyethylene and calcium carbonate fillers is extruded onto a carded nonwoven to form an extrusion laminate. The extrusion laminate is then mechanically stretched to impart breathability in the microporous breathable film. The nonwoven has two surfaces: a film facing surface and an exposed surface opposite to the film facing surface. The printing and coating are made on the exposed surface of the nonwoven. The rest of conditions are the same as Example 2.

Example 4

A spunbonded nonwoven web comprising polypropylene fibers with basis weight of 33 g/m² is used as a substrate web. The nonwoven web is printed with a red based ink, a blue based ink, and a yellow based ink its order. A red based ink composition comprises a first base component and a first hardening component as specified below respectively. A blue base ink composition contains C.I. Pigment Blue 15-4 as a coloring agent instead of C.I. Pigment Red 48-3 of the red based ink composition below while the rest of the components of the blue based ink composition is the same as those of the red based ink composition below. The yellow based ink composition contains C.I. Pigment Yellow 14 as a coloring agent instead of C.I. Pigment Red 48-3 of the red based ink composition below while the rest of the components of the yellow based ink composition is the same as those of the red based ink composition below. The first base component and the first hardening component of each of the red, blue, and yellow based inks are mixed prior to printing to form each color of the ink composition respectively. The nonwoven is printed with the ink composition by using a flexographic printing machinery at a speed of approximately 150 m/min. The amount of the three ink compositions applied is 1.5 g/m². A coating composition comprises a second base component and a second hardening component as specified below respectively. The second base component and the second hardening component are mixed prior to coating to form the coating composition. The ink composition printed on the nonwoven web is coated with the coating composition with 4 g/m². The printed and over coated nonwoven is then dried by evaporating the solvent and is then aged at room temperature (i.e., 25° C.) for 24 hours.

| Ink Composition | | |
|---|---|---|
| First base component | | 80% |
| First hardening component | | 20% |
| First base component | | |
| Binder Polymer | Polyurethane resin | 5.0% |
| | Polyvinyl butyral rein | 7.5% |
| Coloring Agent | C.I. Pigment Red 48-3 | 10.0% |
| Solvent | 1-propanol | 41.6% |
| | 2-Propanol | 1.2% |
| | Ethyl acetate | 4.7% |
| | Propyl acetate | 20.5% |
| | Ethyl alcohol | 2.6% |
| Additives | Polyethylene wax | 3.3% |
| | Cellulose Nitrate | 0.6% |
| | Shellac | 3.0% |
| First hardening component | | |
| Hardener | Polyisocyanate | 37.5% |
| Solvent | Ethyl acetate | 5% |

| Coating Composition | | |
|---|---|---|
| Second base component | | 80% |
| Second hardening component | | 20% |
| Second base component | | |
| Binder Polymer | Polyurethane resin | 12.5% |
| | Polyvinyl butyral resin | 8.0% |
| Solvent | 1-propanol | 14.1% |
| | 2-Propanol | 51.4% |
| | Ethyl acetate | 2.7% |
| | Propyl acetate | 6.9% |
| Additives | Polyethylene wax | 3.4% |
| | Silica | 1.0% |
| Second hardening component | | |
| Hardener | Polyisocyanate | 37.5% |
| Solvent | Ethyl acetate | 62.5% |

Example 5

A spunbonded nonwoven web comprising polypropylene fibers with basis weight of 33 g/m² is used as a substrate web.

The nonwoven web is printed with a red based ink, a blue based ink, and a yellow based ink in its order. A red based ink composition comprises a first base component as specified below. A blue base ink composition contains C.I. Pigment Blue 15-4 as a coloring agent instead of C.I. Pigment Red 48-3 of the red based ink composition below while the rest of the components of the blue based ink composition is the same as those of the red based ink composition below. The yellow based ink composition contains C.I. Pigment Yellow 14 as a coloring agent instead of C.I. Pigment Red 48-3 of the red based ink composition below while the rest of the components of the yellow based ink composition is the same as those of the red based ink composition below. The nonwoven is printed with the ink composition by using a flexographic printing machinery at a speed of approximately 150 m/min. The amount of the three ink compositions applied is 1 g/m². A coating composition comprises a second base component and a second hardening component as specified below respectively. The second base component and the second hardening component are mixed prior to coating to form the coating composition. The ink composition printed on the nonwoven web is coated with the coating composition with 1.5 g/m².

The printed and over coated nonwoven is then dried by evaporating the solvent and is then aged at room temperature (i.e., 25° C.) for 24 hours.

| Ink Composition | | |
| --- | --- | --- |
| First base component | | 100% |
| First base component | | |
| Binder Polymer | Polyurethane resin | 5.0% |
| | Polyvinyl butyral rein | 7.5% |
| Coloring Agent | C.I. Pigment Red 48-3 | 10.0% |
| Solvent | 1-propanol | 41.6% |
| | 2-Propanol | 1.2% |
| | Ethyl acetate | 4.7% |
| | Propyl acetate | 20.5% |
| | Ethyl alcohol | 2.6% |
| Additives | Polyethylene wax | 3.3% |
| | Cellulose Nitrate | 0.6% |
| | Shellac | 3.0% |

| Coating Composition | | |
| --- | --- | --- |
| Second base component | | 90% |
| Second hardening component | | 10% |
| Second base component | | |
| Binder Polymer | Polyurethane resin | 12.5% |
| | Polyvinyl butyral resin | 8.0% |
| Solvent | 1-propanol | 14.1% |
| | 2-Propanol | 51.4% |
| | Ethyl acetate | 2.7% |
| | Propyl acetate | 6.9% |
| Additives | Polyethylene wax | 3.4% |
| | Silica | 1.0% |
| Second hardening component | | |
| Hardener | Polyisocyanate | 37.5% |
| Solvent | Ethyl acetate | 62.5% |

Example 6

The nonwoven web of Example 5 is continuously supplied and applied with corona discharging treatment by Sherman Corona Treater supplied by Sherman Treaters at the corona discharging power of 58 W·m²/min, before being printed with an ink composition. Then the corona treated nonwoven web is printed with an ink composition. The rest of conditions are the same as Example 5.

Example 7

A spunbonded nonwoven web comprising polypropylene fibers with basis weight of 33 g/m² is used as a substrate web. The nonwoven web is printed with a red based ink, a blue based ink, and a yellow based ink in its order. A red based ink composition comprises a first base component and a first hardening component as specified below respectively. A blue base ink composition contains C.I. Pigment Blue 15-4 as a coloring agent instead of C.I. Pigment Red 48-3 of the red based ink composition below while the rest of the components of the blue based ink composition is the same as those of the red based ink composition below. The yellow based ink composition contains C.I. Pigment Yellow 14 as a coloring agent instead of C.I. Pigment Red 48-3 of the red based ink composition below while the rest of the components of the yellow based ink composition is the same as those of the red based ink composition below. The first base component and the first hardening component of each of the red based, the blue based and the yellow based inks are mixed prior to printing to form each color of the ink composition respectively. The nonwoven is printed with the ink composition by using a flexographic printing machinery at a speed of approximately 150 m/min. The amount of the three ink compositions applied is 1 g/m². A coating composition comprises a second base component as specified below respectively. The ink composition printed on the nonwoven web is coated with the coating composition with 2 g/m². The printed and over coated nonwoven is then dried by evaporating the solvent and is then aged at room temperature (i.e., 25° C.) for 24 hours.

| Ink Composition | | |
| --- | --- | --- |
| First base component | | 90% |
| First hardening component | | 10% |
| First base component | | |
| Binder Polymer | Polyurethane resin | 5.0% |
| | Polyvinyl butyral rein | 7.5% |
| Coloring Agent | C.I. Pigment Red 48-3 | 10.0% |
| Solvent | 1-propanol | 41.6% |
| | 2-Propanol | 1.2% |
| | Ethyl acetate | 4.7% |
| | Propyl acetate | 20.5% |
| | Ethyl alcohol | 2.6% |
| Additives | Polyethylene wax | 3.3% |
| | Cellulose Nitrate | 0.6% |
| | Shellac | 3.0% |
| First hardening component | | |
| Hardener | Polyisocyanate | 37.5% |
| Solvent | Ethyl acetate | 62.5% |

| Coating Composition | | |
| --- | --- | --- |
| Second base component | | 100% |
| Second base component | | |
| Binder Polymer | Polyurethane resin | 12.5% |
| | Polyvinyl butyral resin | 8.0% |
| Solvent | 1-propanol | 14.1% |
| | 2-Propanol | 51.4% |

| Coating Composition | | |
|---|---|---|
| Additives | Ethyl acetate | 2.7% |
| | Propyl acetate | 6.9% |
| | Polyethylene wax | 3.4% |
| | Silica | 1.0% |

Example 8

The nonwoven web of Example 7 is continuously supplied and applied with corona discharging treatment by Sherman Corona Treater supplied by Sherman Treaters at the corona discharging power of 58 W·m²/min, before being printed with an ink composition. Then the corona treated nonwoven web is printed with an ink composition. The rest of conditions are the same as Example 7.

Example 9

A spunbonded nonwoven web comprising polypropylene fibers with basis weight of 33 g/m² is used as a substrate web. It is continuously supplied and applied with corona discharging treatment by Sherman Corona Treater supplied by Sherman Treaters at the corona discharging power of 58 W·m²/min. An ink composition is a red based ink composition and comprises a first base component and a first hardening component as specified below respectively. The first base component and the first hardening component are mixed prior to printing to form the ink composition. The corona treated nonwoven is printed with the ink composition by using a flexographic printing machinery at a speed of approximately 150 m/min. The amount of the ink composition applied is 2 g/m². A coating composition comprises a second base component and a second hardening component as specified below respectively. The second base component and the second hardening component are mixed prior to coating to form the coating composition. The ink composition printed on the nonwoven web is coated with the coating composition with 3 g/m². The printed and over coated nonwoven is then dried by evaporating the solvent and is then aged at room temperature (i.e., 25° C.) for 24 hours.

| Ink Composition | | |
|---|---|---|
| First base component | | 80% |
| First hardening component | | 20% |
| First base component | | |
| Binder Polymer | Polyurethane resin | 15.5% |
| Coloring Agent | C.I Pigment Red 48-3 | 10.0% |
| Solvent | 1-propanol | 27.1% |
| | 2-Propanol | 18.2% |
| | Ethyl acetate | 4.7% |
| | Propyl acetate | 20.6% |
| Additives | Polyethylene wax | 3.3% |
| | Cellulose Nitrate | 0.6% |
| First hardening component | | |
| Hardener | Polyisocyanate | 37.5% |
| Solvent | Ethyl acetate | 62.5% |

| Coating Composition | | |
|---|---|---|
| Second base component | | 90% |
| Second hardening component | | 10% |
| Second base component | | |
| Binder Polymer | Polyurethane resin | 22.0% |
| Solvent | 1-propanol | 21.1% |
| | 2-Propanol | 27.3% |
| | Ethyl acetate | 3.7% |
| | Propyl acetate | 21.3% |
| Additives | Polyethylene wax | 3.6% |
| | Silica | 1.0% |
| Second hardening component | | |
| Hardener | Polyisocyanate | 37.5% |
| Solvent | Ethyl acetate | 62.5% |

Example 10

A spunbonded nonwoven web comprising polypropylene fibers with basis weight of 33 g/m² is used as a substrate web. It is continuously supplied and applied with corona discharging treatment by Sherman Corona Treater supplied by Sherman Treaters at the corona discharging power of 58 W·m²/min. An ink composition is a red based ink composition and comprises a first base component and a first hardening component as specified below respectively. The first base component and the first hardening component are mixed prior to printing to form the ink composition. The corona treated nonwoven is printed with the ink composition by using a flexographic printing machinery at a speed of approximately 150 m/min. The amount of the ink composition applied is 1 g/m². A coating composition comprises a second base component and a second hardening component as specified below respectively. The second base component and the second hardening component are mixed prior to coating to form the coating composition. The ink composition printed on the nonwoven web is coated with the coating composition with 1 g/m². The printed and over coated nonwoven is then dried by evaporating the solvent and is then aged at room temperature (i.e., 25° C.) for 24 hours.

| Ink Composition | | |
|---|---|---|
| First base component | | 90% |
| First hardening component | | 10% |
| First base component | | |
| Binder Polymer | Polyurethane resin | 29.0% |
| Coloring Agent | C.I. Pigment Red 48-3 | 10.0% |
| Solvent | 1-propanol | 11.5% |
| | 2-Propanol | 12.9% |
| | Ethyl acetate | 12.1% |
| | Propyl acetate | 9.0% |
| | Propylene glycol monomethyl ether | 5.7% |
| | Propyl glycol | 5.0% |
| Additives | Polyethylene wax | 3.6% |
| | Cellulose Nitrate | 1.2% |
| First hardening component | | |
| Hardener | Polyisocyanate | 37.5% |
| Solvent | Ethyl acetate | 62.5% |

| Coating Composition | | |
|---|---|---|
| Second base component | | 90% |
| Second hardening component | | 10% |
| Second base component | | |
| Binder Polymer | Polyurethane resin | 32.0% |
| Solvent | 1-propanol | 12.8% |
| | 2-Propanol | 15.4% |
| | Ethyl acetate | 15.7% |
| | Propyl acetate | 9.0% |
| | Propylene glycol monomethyl ether | 5.3% |
| | Propyl glycol | 5.0% |
| Additives | Polyethylene wax | 3.6% |
| | Silica | 1.2% |
| Second hardening component | | |
| Hardener | Polyisocyanate | 37.5% |
| Solvent | Ethyl acetate | 62.5% |

Statements of Incorporation by Reference and Intended Scope of Claims

The disclosures of all patents, patent applications and any patents which issue thereon, as well as any corresponding published foreign patent applications, and all publications listed and/or referenced in this description, are hereby incorporated herein by reference. It is expressly not admitted that any of the documents or any combination of the documents incorporated herein by reference teaches or discloses the present invention. To the extent that any meaning or definition of a term in this document conflicts with any meaning or definition of the same term in a document incorporated by reference, the meaning or definition assigned to that term in this document shall govern.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

While particular embodiments of the present invention have been illustrated and described, it would be obvious to those skilled in the art that various changes and modifications can be made without departing from the spirit and scope of the invention. It is therefore intended to cover in the claims all such changes and modifications that are within the scope of this invention.

What is claimed is:

1. A disposable diaper comprising:
a liquid permeable topsheet;
a liquid impermeable backsheet; and
an absorbent core disposed between the topsheet and the backsheet,
the backsheet comprising an ink-printed substrate web comprising a laminate of a polymeric film web and a synthetic nonwoven web, the film web being disposed adjacent to the absorbent core and the nonwoven web being disposed opposite the absorbent core, the nonwoven web having a surface facing toward the polymeric film web and an opposing outer surface;
an ink composition forming an ink film on the outer surface of the nonwoven web; and
a coating composition forming a coating film on the ink film and thereby sandwiching the ink film between the coating film and the nonwoven web,
wherein at least the ink composition forms a first ink composition cross-linked structure within the ink film and forms a first intercomposition cross-linked structure with the coating composition between the ink film and the coating film, or the coating composition forms a first coating composition cross-linked structure within the coating film and forms the first intercomposition cross-linked structure with the ink composition between the coating film and the ink film.

2. The disposable diaper of claim 1 wherein the synthetic nonwoven web is made of a polyolefin.

3. The disposable diaper of claim 1 wherein the coating composition forms the first coating composition cross-linked structure within the coating film and forms the first intercomposition cross-linked structure with the ink composition between the coating film and the ink film.

4. The disposable diaper of claim 1 wherein the ink composition forms the first ink composition cross-linked structure within the ink film and forms the first intercomposition cross-linked structure with the coating composition between the ink film and the coating film.

5. The disposable diaper of claim 1 wherein the ink composition forms the first ink composition cross-linked structure within the ink film, the coating composition forms the first coating composition cross-linked structure within the coating film, the ink composition forms the first intercomposition cross-linked structure with the coating composition between the ink film and the coating film, and the coating composition forms a second intercomposition cross-linked structure with the ink composition between the coating film and the ink film.

6. The disposable diaper of claim 1 wherein the ink composition comprises an ink composition binder polymer and an ink composition hardener forming the first ink composition cross-linked structure with the ink composition hardener and forming the first intercomposition cross-linked structure with a coating composition binder polymer, or the coating composition comprises a coating composition binder polymer and a coating composition hardener forming the first coating composition cross-linked structure and forming the first intercomposition cross-linked structure with an ink composition binder polymer.

7. The disposable diaper of claim 1 wherein the ink composition comprises an ink composition binder polymer and a coloring agent, the coating composition comprises a coating composition binder polymer and a coating composition hardener, and the coating composition hardener forms the first coating composition cross-linked structure with the coating composition binder polymer and forms the first intercomposition cross-linked structure with the ink composition binder polymer.

8. The disposable diaper of claim 1 wherein the ink composition comprises an ink composition binder polymer, an ink composition hardener and a coloring agent, the coating composition comprises a coating composition binder polymer, and the ink composition hardener forms the first ink composition cross-linked structure with the ink composition binder polymer and forms the first intercomposition cross-linked structure with the coating composition binder polymer.

9. The disposable diaper of claim 1 wherein the ink composition comprises a first binder polymer, a first hardener and a coloring agent, the coating composition comprises a second binder polymer and a second hardener, the first hardener forms a cross-linked structure with the first binder polymer and the second binder polymer, and the second hardener forms a cross-linked structure with the first binder polymer and the second binder polymer.

10. The disposable diaper of claim 1 wherein an ink rub-off amount of an ink-printed area of the ink-printed substrate web is not more than about 0.05 mg/cm².

11. A disposable diaper comprising:
a liquid permeable topsheet;
a liquid impermeable backsheet; and
an absorbent core disposed between the topsheet and the backsheet,
the backsheet comprising an ink-printed substrate web comprising a laminate of a polymeric film web and a synthetic nonwoven web, the film web being disposed adjacent to the absorbent core and the nonwoven web being disposed opposite the absorbent core, the nonwoven web having a surface facing toward the polymeric film web and an opposing outer surface;
an ink composition forming an ink film on the outer surface of the nonwoven web; and
a coating composition forming a coating film on the ink film and thereby sandwiching the ink film between the coating film and the nonwoven web,
wherein the ink composition forms an ink composition cross-linked structure within the ink film and the coating composition forms a coating composition cross-linked structure within the coating film.

12. The disposable diaper of claim 11 wherein the ink composition comprises an ink composition binder polymer, an ink composition hardener, and a coloring agent, the coating composition comprises a coating composition binder polymer, and a coating composition hardener, the ink composition hardener forms the ink composition cross-linked structure with the ink composition binder, and the coating composition hardener forms the coating composition cross-linked structure with the coating composition binder.

* * * * *

UNITED STATES PATENT AND TRADEMARK OFFICE
CERTIFICATE OF CORRECTION

PATENT NO. : 7,416,777 B2 Page 1 of 1
APPLICATION NO. : 11/713530
DATED : August 26, 2008
INVENTOR(S) : Nair et al.

It is certified that error appears in the above-identified patent and that said Letters Patent is hereby corrected as shown below:

Column 20
Line 31, delete "rein" and insert --resin--.
Line 41, delete "5%" and insert --62.5%--.
Column 21
Line 34, delete "rein" and insert --resin--.
Column 22
Line 43, delete "rein" and insert --resin--.

Signed and Sealed this

Second Day of June, 2009

JOHN DOLL
*Acting Director of the United States Patent and Trademark Office*